United States Patent
Park et al.

(10) Patent No.: US 6,217,912 B1
(45) Date of Patent: Apr. 17, 2001

(54) POLYESTER ANALOGUE OF POLY-L-LYSINE AS A SOLUBLE, BIODEGRADABLE GENE DELIVERY CARRIER

(75) Inventors: Jong Sang Park; Young Hun Choi, both of Seoul (KR); Sung Wan Kim, Salt Lake City, UT (US)

(73) Assignee: Expression Genetics, Inc., Salt Lake City, UT (US)

( * ) Notice: Subject to any disclaimer, the term of this patent is extended or adjusted under 35 U.S.C. 154(b) by 0 days.

(21) Appl. No.: 09/352,473

(22) Filed: Jul. 13, 1999

Related U.S. Application Data (60) Provisional application No. 60/092,682, filed on Jul. 13, 1998.

(51) Int. Cl.$^7$ ............................ A61K 47/14; A61K 48/00; C12N 15/85; C12N 15/00

(52) U.S. Cl. ........................... 424/501; 424/489; 435/325; 435/440; 514/44

(58) Field of Search ..................... 435/6, 325, 440; 424/501, 489; 514/44

(56) References Cited

U.S. PATENT DOCUMENTS 5,942,253 * 8/1999 Gombotz et al. .................... 424/501

* cited by examiner

*Primary Examiner*—John S. Brusca
*Assistant Examiner*—Mark L. Shibuya
(74) *Attorney, Agent, or Firm*—Thorpe North & Western, LLP (57) ABSTRACT

Poly[α-(4-aminobutyl)-L-glycolic acid] (PAGA) is disclosed as a biodegradable composition suitable for delivering a gene into a cell. Methods of making and using PAGA are also disclosed.

41 Claims, 7 Drawing Sheets

PLL

POLYESTER ANALOGUE OF POLY-L-LYSINE AS A SOLUBLE, BIODEGRADABLE GENE DELIVERY CARRIER

CROSS-REFERENCE TO PRIOR APPLICATION UNDER 35 U.S.C. §119

This application claims the benefit of U.S. Provisional Application No. 60/092,682 filed Jul. 13, 1998.

BACKGROUND OF THE INVENTION

This invention relates to gene therapy and drug delivery. More particularly, the invention relates to compositions and methods for use, and making thereof, for delivering nucleic acids as gene therapy applications or other non-soluble bioactive molecules such as protein, peptides or small non-soluble drugs.

Biodegradable polymers are gaining attention as drug delivery systems. R. Langer, New Methods of Drug delivery, 249 Science 1527–1533 (1990); B. Jeong et al., Biodegradable Block Copolymers as Injectable Drug-delivery Systems, 388 Nature 860–862 (1997). Since genes are now considered pharmaceutical agents for treating many types of diseases, and gene therapy is becoming widely used as demonstrated by many clinical trials, M. A. Kay et al., Gene Therapy, 94 Proc. Nat'l Acad. Sci. USA 1744–12746 (1997); C. Bordignon et al., Gene Therapy in Peripheral Blood Lymphocytes and Bone Marrow for ADA-immunodeficient Patients, 270 Science 470–475 (1995), there is an urgent need for a safe and efficient gene carrier. Genes are very attractive candidates for therapeutic use in a variety of disease states due to their ability to produce bioactive proteins using the biosynthetic machinery provided by host cells. A major technical impediment to gene transfer is the lack of an ideal gene delivery system. There are many established protocols for transferring genes into cells, including calcium phosphate precipitation, electroporation, particle bombardment, liposomal delivery, viral-vector delivery, and receptor-mediated gene delivery. A.V.Kavanov, Self-assembling Complexes for Gene delivery, p.L.Felgner & L.W.Seymour, J.Wiley & Sons (1998); P.L.Chang, Somatic Gene Therapy, CRC Press (1995).

Transfection methods using retroviral or adenoviral vectors have been investigated. Retroviral vectors, in particular, have been used successfully for introducing exogenous genes into the genomes of actively dividing cells such that stable transformants are obtained. D. G. Miller et al., Gene Transfer by Retrovirus Vectors Occurs Only in Cells that are Actively Replicating at the Time of Infection. 10 Mol. Cell Biol. 4239–4242 (1990). Viral vector systems often, in case of complementation of defective vectors by inserting genes into 'helper' cell lines, generate a transducing infectious agent. In addition, it is well known that the host immune response to adenoviruses limits their use as a transfer facilitating agent to a single administration. To address this limitation, fusion peptides of the influenza virus hemagglutinin have been employed to replace adenoviruses as endosomal lytic agents, but have met with limited success. S. Gottschalk et al., A Novel DNA-Peptide Complex for Efficient Gene Transfer and Expression in Mammalian Cells, 3 Gene Ther. 448–457 (1996). However, despite their high transfection efficiency in vitro, inserting genes into the host cell's genome in vivo depends on the viral infection pathway. Application of the viral infection pathway for human gene therapy introduces serious concerns about endogenous virus recombination, oncogenic effects, and inflammatory or immunologic reactions. G Ross et al., Gene Therapy in the United States: A Five-Year Status Report. 7 Hum. Gene Ther., 1781–1790 (1996). Because of these concerns the use of viral vectors for human gene therapy has been extremely limited.

As compared to viral gene carriers, there are several advantages to the use of non-viral based gene therapies, including their relative safety and low cost of manufacture. Non-viral gene delivery systems such as cationic liposomes or synthetic gene carriers, e.g.poly-L-lysine (PLL), are being widely sought as alternatives and investigated intensively to circumvent some problems encountered in viral vectors. K. A. Mislick et al., Transfection of Folate-polylysine DNA Complexes: Evidence for Lysosomal Delivery, 6 Bioconjugate Chem. 512–515 (1995); J.O. Rädler et al., Structure of DNA-cationic Liposome Complexes: DNA Intercalation in Multilamellar Membranes in Distinct Interhelical Packing Regimes, 275 Science 810–814 (1997); J. Cheng et al., Effect of Size and Serum Proteins on Transfection Efficiency of Poly((2-dimethylamino)ethyl methacrylate)-plasmid nanoparticles, 13 Pharm. Res. 1038–1042 (1996). There are several polymeric materials currently being investigated for use as gene carriers, of which poly-L-lysine (PLL)is the most popular, but few of them are biodegradable. Biodegradable polymers, such as polylactic/glycolic acid (negatively charged), and polylactide/glycolide (neutral) have been used as gene carriers in the form of non-soluble particulates. Amarucyama et al, Nanoparticle DNA Carrier with PLL Grafted Polysallanide Copolymer and Polylactic Acid, 8 Bioconjugate, 735–739(1997). In general, polycationinic polymers are known to be toxic and the PLL backbone is barely degraded under physiological conditions. It will remain in cells and tissue which cause undesirably high toxicity. A.Segouras & R.Dunlan, Methods for Evaluation of Biocompatibility of Synthetic Polymers, 1 J.Mater.Sci in Medicine, 61–68(1990).

In view of the foregoing it will be appreciated that providing a soluble and biodegradable gene carrier, meaning that the polymer gene carrier can break down or degrade within body to non-toxic components after the genes have been delivered, that is non viral, safe and effective would be a significant advancement in the art.

BRIEF SUMMARY OF THE INVENTION

It is an object of the present invention to provide a composition and a method for delivering nucleic acids into cells.

It is also an object of the present invention to provide a biodegradable gene carrier composition and methods of use and making thereof.

It is another object of the present invention to provide a composition and a method for gene delivery that is efficient and non toxic.

It is yet another object of the invention to provide an non-toxic, soluble, biodegradable, non-viral composition and a method of use thereof, for delivering exogenous nucleic acids into a target cell.

These and other objects can be achieved by providing a novel polymer, poly[α-(4-aminobutyl)-L-glycolic acid] (PAGA), containing a biodegradable ester linkage backbone with positively charged amine groups.

A composition for use as a gene delivery carrier comprises an effective amount of PAGA admixed with an effective amount of a nucleic acid comprising the gene to be delivered.

A method for making poly[α-(4-aminobutyl)-L-glycolic acid] comprises the steps of:

(a) protecting the ∈-amino group of L-lysine with an amine blocking agent to result in blocked L-lysine;

(b) deaminating the α-amino group of the blocked L-lysine to result in blocked (α-amino-2(S)-hydroxyhexanoic acid);

(c) polymerizing the blocked (6-amino-2(S)-hydroxyhexanoic acid) to result in blocked poly[α-(4-aminobutyl)-L-glycolic acid]; and (d) deprotecting the blocked poly[α-(4-aminobutyl)-L-glycolic acid] by removing the amine blocking group to result in poly[α-(4-aminobutyl)-L-glycolic acid].

A method of delivering a selected nucleic acid into a selected cell comprises the steps of:

(a) mixing an effective amount of the selected nucleic acid with an effective amount of poly[α-(4-aminobutyl)-L-glycolic acid] to result in a complex;

(b) contacting the selected cell with the complex under conditions suitable to maintain the viability of the cell.

The biodegradable gene carrier of this invention, PAGA, which is an analogue of PLL, can also be grafted with polyethylene glycol (PEG), which in turn may covalently bind to a targeting moiety by a similar process as disclosed in a copending U.S. patent application, Ser. No. 09/315,240 filed May 20, 1999, which is fully incorporated herein.

DETAILED DESCRIPTION

Before the present biodegradable gene carrier composition and methods of making and using thereof are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise.

Herein there is described an analogue of PLL, poly[α-(4-aminobutyl)-L-glycolic acid] (PAGA), that has an ester backbone. Unlike PLL, PAGA degrades very rapidly under physiological conditions. The polymer has similar capabilities for condensing DNA into a compact form, and its transfection efficiency is even greater than that of PLL. PAGA, therefore, constitutes a non-toxic biodegradable gene carrier.

As used herein, "PLL" refers to poly(L-lysine), derivatives thereof, and mixtures thereof. The PLL preferably has a molecular weight in the range of about 200 to 50,000 and more preferable in the range of 500 to 30,000.

"PAGA" means poly[α-(4-aminobutyl)-L-glycolic acid], which has an ester backbone. PAGA is a non-toxic, water soluble, cationic biodegradable polymer with strong capabilities for condensing nucleic acids and providing for efficient transfection into cells. Preferably, the molecular weight of PAGA according to this invention is within a range of about 4000 to 100,000 daltons.

As used herein, "poly(oxyalkyl)glycol" refers to polyether glycol polymers that can be grafted to PGA or PLL. Each monomer portion of the polymer contains a carbon chain having up to about 5 carbon atoms. Preferred poly(oxyalkyl) glycols are selected from the group consisting of polyethylene glycol (PEG) homopolymers, polypropylene glycol homopolymers, alpha-substituted poly(oxyalkyl) glycols (such as methoxypolyethylene glycols or other suitable alkyl-substituted derivatives such as those containing $C_1$–$C_4$ alkyl groups), poly(oxyalkyl) glycol copolymers and block copolymers, and activated derivatives thereof. The poly(oxyalkyl) glycols used in the present invention preferably have a molecular weight of about 200 to 50,000, and more preferably about 200 to 20,000. An especially preferred poly(oxyalkyl) glycol is polyethylene glycol (PEG). PEG is preferred because it is inexpensive, it is approved by the U.S. Food and Drug Administration for administration to humans, and it is resistant to eliciting an antibody response.

As used herein, "effective amount" means an amount of a nucleic acid that is nontoxic but sufficient to provide the selected local or systemic effect and performance at a reasonable benefit/risk ratio that would attend any medical treatment.

As used herein, "administering", and similar terms mean delivering the complex formed by admixing the nucleic acid to be delivered with a gene carrier composition, according to the present invention, to the individual being treated such that the complex is capable of being circulated systemically to the parts of the body where the complex can contact the target cells. Thus, the composition is preferably administered to the individual by systemic administration, typically by subcutaneous, intramuscular, intravenous, or intraperitoneal administration. Injectable formulations for such use can be prepared in conventional forms, either as a liquid solution or suspension or in a solid form suitable for preparation as a solution or suspension in a liquid prior to injection, or as an emulsion. Suitable excipients include, for example, water, saline, dextrose, glycerol, ethanol, and the like; and if desired, minor amounts of auxiliary substances such as wetting or emulsifying agents, buffers, and the like can also be added.

This invention relates to a novel PLL analogue, PAGA, which is non-toxic and biodegradable and capable of forming stable, soluble complexes with nucleic acids, and the method of preparation thereof. Optionally, PAGA can be covalently bound to PEG, and a targeting moiety(TM) that is recognizable by cell membrane receptors. PAGA is capable of forming complexes with nucleic acids which, upon dissociation, release the nucleic acid to transfect several types of cells, the targeting moiety(TM) makes the transfection selective to cells containing the receptors of the TM. This invention also provides a method for specific cell transfection in vitro or in vivo. After effectively delivering nucleic acids to a targeted cell, the PAGA carrier can be degraded to non-toxic small units under physiological conditions. Therefore, compared to PLL, PAGA of the present invention significantly advances the art of targeted gene delivery.

The invention, in one of its most general definitions, concerns a novel PLL analogue PAGA, and a complex between at least one negatively charged nucleic acid and the positively charged biodegradable PAGA, the association between the nucleic acid and the PAGA polymer being electrostatic in nature. Preferably, the biodegradable PAGA polymer further binds to a PEG polymer, which in turn also binds to a targeting moiety. The addition of PEG prevents the precipitation and aggregation of the complexes (or nanoparticles) formed by PEG-PLL and nucleic acids, thus increasing the solubility of the complexes. The PEG linked to PLL also functions to fuse the cell membranes and prevents the proteolytic degradation of the nucleic acids, thus increasing the transfection efficiency. Furthermore, since PEG can serve as a linker connecting the PLL dendrimer and the targeting moiety(TM) it increases the targeting efficiency of the complexes. The targeting moiety can also be directly bound to PAGA itself. The methods for binding PEG and/or TM to PAGA are similar to those used in grafting PLL and are previously disclosed in copending U.S. Patent application, TNW docket NO.T6624.NP, herein fully incorporated. This invention relates to synthesizing a novel PLL analogue, poly [α-(4-aminobutyl)-L-glycolic acid] (PAGA), containing both a degradable ester linkage and a positively charged backbone. This polymer is capable of binding a nucleic acid and form a compact complex which can be used as a gene carrier. After releasing the nucleic acids into the cell to be transfected, the polymer is then rapidly hydrolytically degraded into non-toxic small units. Furthermore, the PAGA/DNA complex exhibits higher transfection efficiency than that of the PLL/DNA complex. The PAGA/DNA complex also has no toxicity as is shown with PLL/DNA complex. Therefore, the newly designed PAGA can be substituted for PLL gene carriers and for other positively charged polymers, giving increased transfection efficiency and no toxicity.

Figure 1:
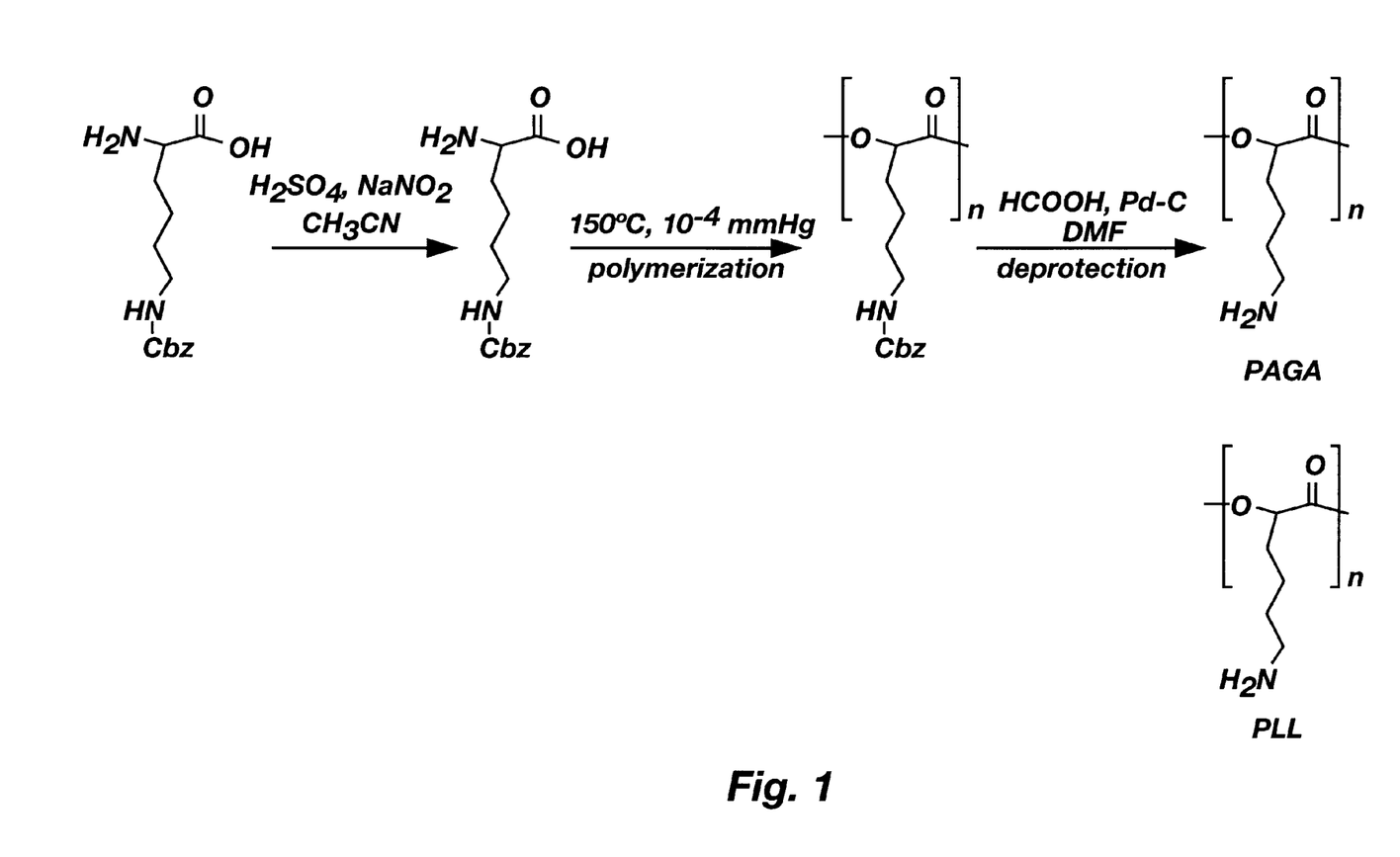
FIG. 1 shows an illustrative synthetic scheme for making poly[α-(4-aminobutyl)-L-glycolic acid] (PAGA); (i) $H_2SO_4$, $NaNO_2$, $CH_3CN$ (54%); (ii) polymerization at 150° C., 10–4 mmHg (96%); (iii) HCOOH, Pd-C, DMF (65%). The structure of poly-L-lysine (PLL) is shown for comparison.

FIG. 1 illustrates the synthesis scheme of PAGA, a PLL analogue having an ester backbone. L-lysine is protected at the ∈-amino group with an amine blocking group, such as a carbobenzoxy (Cbz) group, according to methods well known in the art. The resulting protected amino acid is then deaminated at the α-amino group resulting in a hydroxyl group at that position. These monomers are polymerized by melting condensation polymerization, which is a common process known to one skilled in the art, without the use of a heavy metal catalyst, to reduce the possibility of toxicity arising therefrom. Furthermore, since the only reactant in the polymerization reaction is the monomer, no product that may be harmful to living cells are produced. The polymer is then deprotected by removal of the amine blocking group, resulting in PAGA.

The PAGA of this invention has an overall positive charge that forms a stable complex with nucleic acids. The complex formed is spherical, in size of from 1 μm to 150–250 nm, which is the optimal size for cellular uptake by endocytosis. 12. Choi et al. PEG grafted poly-L-Lysines as polymeric gene carrier. 54 J. Control. Rel. 39–48 (1998). The PAGA is easily biodegradable in physiological conditions, but has a slower and more desirable degradation rate when it forms complexes with nucleic acids. The transfection efficacy of PAGA/DNA is about twice that compared to PLL/DNA. In addition, the PAGA is non-toxic as compared to the currently used PLL. The novel feature of PAGA as a gene carrier is that the fast degradation of PAGA releases free DNA in the nucleus so that expression and transfection of DNA can be more effective and the degraded fragments from PAGA are rapidly removed from cellular compartments, followed by excretion or metabolism in the body. Therefore, PAGA is a safe, efficient, and significantly improved gene carrier compared to PLL.

PAGA of this invention can be optionally used to form block copolymers with other pharmaceutically-acceptable oligomers and/or polymers which binds reversibly to a bioactive agent to be delivered. Preferably, such oligomers and/or polymers are polycations. A preferred polycation is poly-L-lysine(PLL). Other potential block copolymers of PAGA of this invention includes polyargine, polyornithine, histones, avidin, protamines and mixed polymers thereof. Biodegradable neutral hydrophobic polymers such as poly α-hydroxy acids may also be utilized to form block copolymers with PAGA. Representative of such poly α-hydroxy acid polymers are members derived or selected from the group consisting of polylactides and poly(lactide-co-glycolides).

A targeting moiety(TM) is optionally bound to the PAGA of this invention, directly, or to PEG which is in turn bound to the PAGA. A TM could be any signal member which is recognizable by a cell membrane receptor. For example, a simple or complex oligoside recognized by membrane lectins, including asialo-oligoside of triantennary lactosamin, asialooligoside of tetraantennary lactosamin, lewis x, sialyl lewis x, sulfated lewis x, oligomannoside, phosphorylated oligomannoside, sulfated oligosaccharide of lactosamin, lactose, galactose, mannose, fucose, glucose, ribose, arabinose, xylose or rhamnose, lactobionic acid, folic acid, and biotin. TM can also be a peptide, including anti-inflammatory peptides, or certain of their fragments that are recognized by vascular cells, for example, intestinal vasodilator polypeptide(IPV); peptide ligands of various integrines; chemotactic factors such as formyl peptides and antagonists; peptide hormones; or natural metabolites such as biotin, tetrahydrofolate, folic acid, or carnitine. Preferably, the TM is a member selected from a group consisting of: lactose, galactose, mannose, fructose, glucose, ribose, arabinose, xylose or rhamnose, peptides, chemotactic factors, hormones, natural metabolites, biotin, tetrahydrofolate, folic acid, lactobionic acid, asialooligosides, oligomannosides, phosphorylated oligomannosides, sulfated oligosaccharide of lactosamin transferrin and asialoglycoprotein.

Delivery of a nucleic acid, i.e. DNA and/or RNA, can be used to achieve expression of a polypeptide or to inhibit expression of a polypeptide through the use of an "antisense" nucleic acid, especially antisense RNA. As used herein, "polypeptide" means a peptide of any length and includes proteins. The term "polypeptide" is used herein without any particular intended size limitation, unless a particular size is otherwise stated. Typical of polypeptides that can be expressed are those selected from the group consisting of oxytocin, vasopressin, adrenocorticotrophic hormone, epidermal growth factor, prolactin, luteinizing hormone releasing hormone, growth hormone, growth hormone releasing factor, insulin-like growth factors, insulin, erythropoietin, obesity protein such as leptin, somatostatin, glucagon, glucagon-like insulinotropic factors, parathyroid hormone, interferon, gastrin, interleukin-2 and other interleukins and lymphokines, tetragastrin, pentagastrin, urogastrin, secretin, calcitonin, enkephalins, endorphins, angiotensins, renin, bradykinin, bacitracins, polymixins, colistins, tyrocidin, gramicidins, and synthetic analogues, modifications, and pharmacologically active fragments thereof, monoclonal antibodies, and vaccines. This group is not to be considered limiting; the only limitation to the peptide or protein drug that may be expressed is functionality. Delivery of DNA and/or RNA is useful in gene therapy, vaccination, and any therapeutic situation in which a nucleic acid or a polypeptide should be administered in vivo. See, for example, U.S. Pat. No. 5,580,859, incorporated here in by reference.

When the nucleic acid is DNA, it can be a DNA sequence that is itself non-replicating, but is inserted into a plasmid wherein the plasmid further comprises a replicator. The DNA may also contain a transcriptional promoter, such as the CMV IEP promoter, which is functional in humans. The DNA can also encode a polymerase for transcribing the DNA. Many expression vectors for expression of a cloned gene in a mammal are known in the art, and many such expression vectors are commercially available, for example, pEUK-C1 (Clontech, Palo Alto, Calif.). A gene of interest can be inserted into such an expression vector using recombinant DNA technology well known in the art. E.g., J. Sambrook et al., Molecular Cloning: A Laboratory Manual (2d ed., 1989), hereby incorporated by reference.

The non-toxic, biodegradable PAGA of the invention can form stable and soluble complexes with nucleic acids which can effectively transfect mammal cells. The nucleic acid can be chosen from the following items: a) gene markers, such as luciferase gene, b-galactosidase gene, chloramphenicol acetyl transferase gene, genes bestowing the resistance to an antibiotic, such as hygromycin or neomycin; b) genes for therapeutic purposes, such as the gene encoding low density lipoprotein receptors deficient in the case of hypercholesterolemia (liver), coagulation factors, gene suppressers of tumors, major histocompatibility proteins, antioncogenes, sense and antisense RNA, and ribozymes; and c) genes with vaccine purposes, such as genes encoding viral antigens.

The method of in vitro or in vivo transfection of the present invention includes the introduction of a complex of nucleic acids and the non-toxic, biodegradable PAGA into a medium containing cells to be transfected under conditions such that there exists: passage of the complex from the medium into the cytoplasm of the cells, release of the nucleic acid of the aforementioned complex into the cytosol of the cells, transcription and expression of the nucleic acid in the transfected cells.

The method can be used for treating a disease associated with a deficiency or absence or mutation of a specific polypeptide. In accordance with another aspect of the invention, the method provides for immunizing an individual, wherein such individual can be a human or an animal, comprising delivering a DNA and/or RNA to the individual wherein the DNA and/or RNA codes for an immunogenic translation product that elicits an immune response against the immunogen. The method can be used to elicit a humoral immune response, a cellular immune response, or a mixture thereof.

The invention also refers to the use of a complex formed by nucleic acids and the polymeric gene carrier according to the invention for the transfection of cells which may be chosen from the following: cells from hematopoietic strains; liver cells; cells of skeletal muscles; skin cells such as fibroblasts, keratinocytes, dendritic cells, or melanocytes; cells of the vascular walls such as endothelial cells or smooth muscle cells; epithelial cells of the respiratory tract; cells of the central nervous system; cancer cells; cells of the immune system, such as lymophocytes, macrophages, NK cells, etc.

Another aspect of the present invention relates to a method of using PAGA as a drug delivery vehicle. The nontoxic, biodegradable and positively charged PAGA can be complexed with negatively charged molecules such as proteins, peptides and other bioactives molecules. PAGA may also be used to make insoluble particulates with drugs, e.g. nanoparticles or microspheres.

An illustrative method of forming the gene carriers according to the present invention is accomplished by synthesizing PAGA, which can be optionally grafted with PEG polymers. The non-toxic, biodegradable PAGA of the present invention can spontaneously form condensed complexes with nuclei acids such as DNA or RNA. The solubility and the transfection efficiency of the complexes increases if the PAGA is PEG grafted. The electrostatic complex is formed by the affinity of the positively-charged polymer (e.g. PAGA) and the negatively-charged nucleic acid. A targeting moiety(TM) is also optionally bound to the PAGA or PEG to specifically direct the gene delivery to the targeted cells.

The following examples are presented to illustrate the process of synthesizing PAGA, the composition of biodegradable gene carrier and method of using the composition of the present invention.

EXAMPLE 1

Synthesis of PAGA

A new monomer, L-oxylysine, was made from L-lysine by converting the α-amino group into a hydroxyl group (FIG. 1.) The monomer was polymerized by melt condensation. There will be no harmful side products from the polymerization as the only reactant is the monomer.

L-lysine is protected at the ∈-amino group with an amine blocking group, such as a carbobenzoxy (Cbz) group, according to methods well known in the art. The resulting protected amino acid is then deaminated at the α-amino group to result in a hydroxyl group at that position. These monomers are polymerized by melt condensation polymerization without the use of a heavy metal catalyst, to reduce the possibility of toxicity arising therefrom. Furthermore, since the only reactant in the polymerization reaction is the monomer, no adducts that may be harmful to living cells are produced. The polymer is then deprotected by removal of the amine blocking group, resulting in PAGA. The difference between PAGA and PLL is only in the backbone bond. An ester bond in PAGA versus an amide bond in PLL.

Matrix-Assisted Laser Desorption/Ionization Time of Flight Mass Spectrometry (MALDI-TOF MS) was used to determine the molecular weights of the degraded positively charged PAGA.

TABLE 1

PAGA degradation data by MALDI-TOF MS

| Time | $M_p{}^a$ | Time | $M_p$ |
|---|---|---|---|
| 0 min | 3207 ± 13.1 | 300 min | 1048 ± 9.3 |
| 30 min | 1600 ± 11.0 | 3 days | 991 ± 11.2 |
| 60 min | 1331 ± 11.4 | 1 month | 969 ± 4.2 |
| 180 min | 1117 ± 4.9 | 6 month | 147 ± 18$^b$ |

PAGA was incubated in pH 7.3 buffer at 37° C.
$^a$The most probable peak molecular weight determined from the highest peak intensity in the MALDI spectrum.
$^b$Molecular weight of the monomer.
Data are mean ± s.e.m. of three different experiments.

EXAMPLE 2

Degradation of PAGA

Figure 2A:
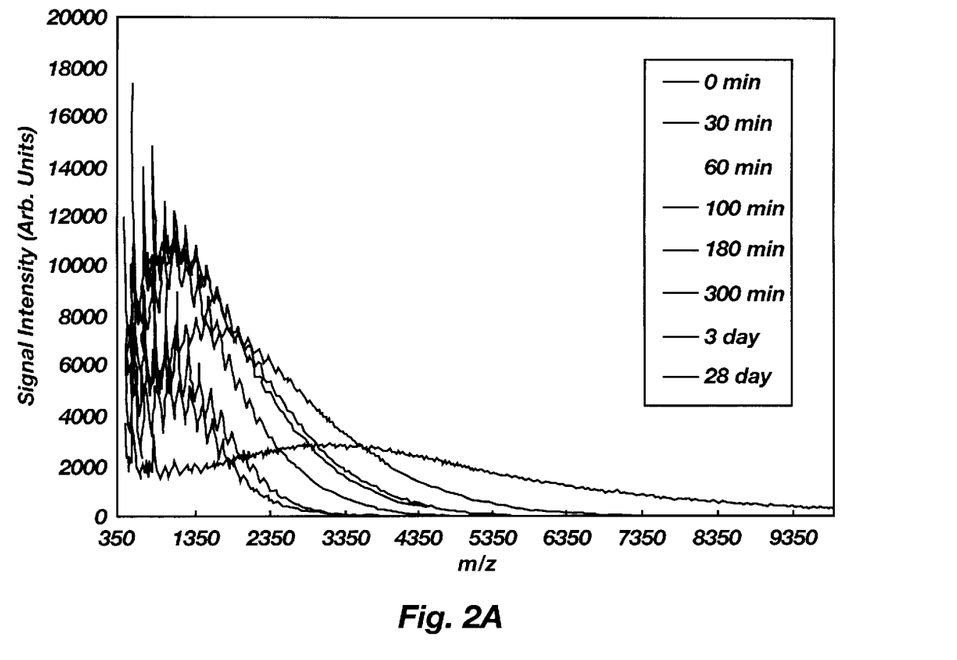
FIG. 2A–B Degradation study of PAGA in an aqueous solution by MALDI-TOF MS; (A) Degradation of PAGA within 3 days and (B) after 6 months. Peaks other than the monomer peak come from matrix, buffer, and salt. The spectra are the sum of 128 laser shots and were 7-point Savitzky-Golay smoothed.
Figure 2B:
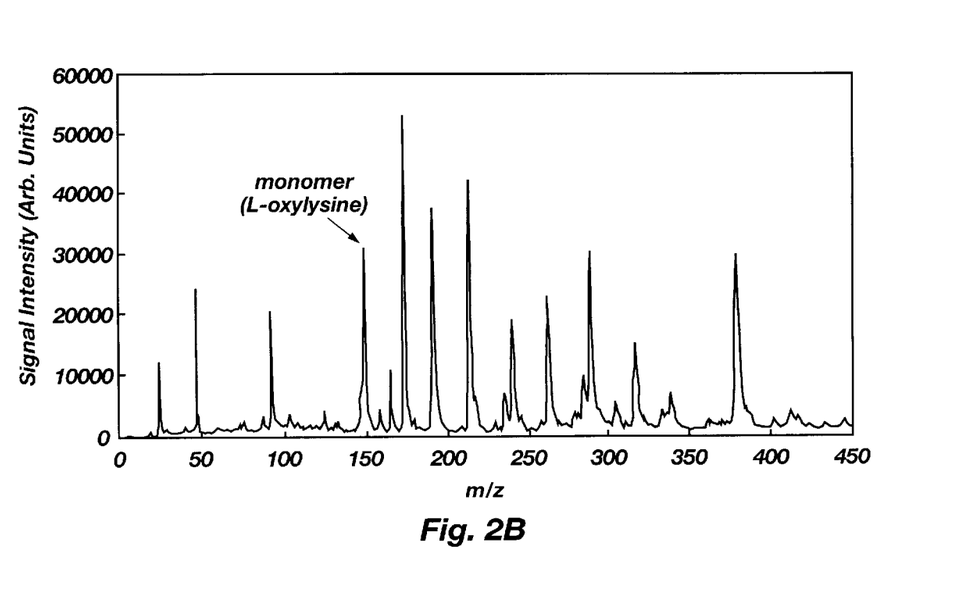

Molecular weight distribution (MWD) and degradation kinetics of PAGA were investigated by Matrix-Assisted Laser Desorption/Ionization Time-of-Flight Mass Spectrometry (MALDI-TOF MS (FIGS. 2A–B and Table 1). PAGA prepared according to the procedure of Example 1 was dissolved in 25 mM HEPES, pH 7.3, at a concentration of 1 nmole (5 mg/ml) and was then incubated at 37° C. The matrix was α-cyano-4-hydroxy cinnamic acid (αCHCA) prepared at a concentration of 10 mg/ml in water/3% TFA/acetonitrile, 4:1:6 (v/v/v). At selected time intervals, a 1 μl aliquot of PAGA solution was added to 9 μl of matrix solution in a microcentrifuge tube. A 1 μl aliquot of this mixture was applied to the MALDI sample plate and dried in a vacuum. An $N_2$ laser radiating at 337 nm with 3-ns pulses was used in a Voyager Biospectrometry Workstation (Perceptive Biosystems). The ions generated by the laser pulses were accelerated to 29 kV energy in the positive-ion mode. All spectra were obtained at the same laser power.

The molecular weight of PAGA after 5 hours of incubation in a buffer solution (pH=7.3) fell to less than 30% compared to that of intact PAGA (FIG. 2A). After 2 hours, degradation of PAGA became very slow. The fast degradation of PAGA seems to result mainly from self-degradation via hydrolysis of the ester linkage by the ∈-amino groups. The polymer was gradually degraded to near completion in 6 months and the final degradation product was the monomer, L-oxylsine (FIG. 2B). Approximately two-thirds of the original polymer was degraded within 5 hours and the polymer was gradually degraded to near completion in 6 months (Table 1). Molecular weights of the degraded polymers are described as $M_p$, the most probable peak molecular weight determination from the highest peak intensity in the MALDI spectrum. The final degradation product was the monomer, L-oxylysine (FIG. 2B). A degradation study was also performed on PLL under the same conditions or in a pseudo-extracellular milieu. Even after 3 months, the PLL had hardly degraded.

EXAMPLE 3

Complex Formation Ability of PAGA with DNA

The DNA condensing ability of PAGA was determined by agarose gel band shift assay (FIGS. 3A–E). PAGA prepared according to the procedure of Example 1 and plasmid DNA (pSV-CAT; Promega, Madison, Wis.) were mixed together in various ratios of positive (PAGA) to negative charges (DNA), and were then were fractionated by agarose gel electrophoresis. With the negative charges of the phosphodiester backbone of DNA, the positive charges of PAGA began to make a strong complex when the positive to negative charges reached a ratio of about 1:1.

Figure 3A:
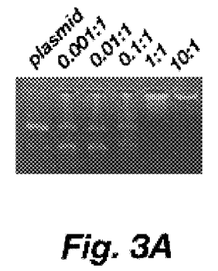
FIGS. 3A–E show an agarose gel band shift assay of selected positive-to-negative charge ratios of PAGA/DNA complexes; control DNA is indicated by "plasmid"; 3B–D shows agarose gel band shift assays of selected positive-to-negative charge ratios of PAGA/DNA complexes after 4, 8, and 24 hours of incubation at 37° C. respectively; 3E shows a control agarose gel band shift assay of selected positive-to-negative charge ratios of PLL/DNA complexes after 4, 8, 24 hours, and 4 days of incubation at 37° C.
Figure 3B:
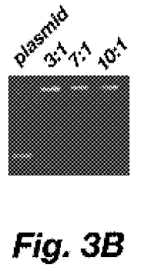
Figure 3C:
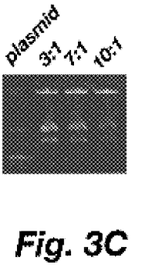
Figure 3D:
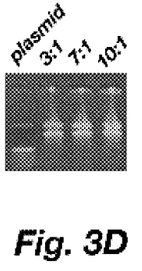
Figure 3E:
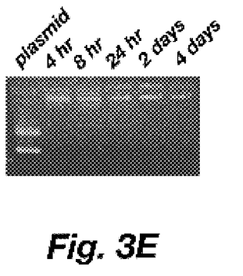

Since PAGA degrades very quickly in solution, it was important to verify that PAGA/DNA complexes are stable enough for transfection to occur. The stability of PAGA/DNA complexes was investigated by measuring the dissociation of DNA from the complex after incubation for selected times at 37° C. FIGS. 3B–D show agarose gel band shift assays of selected positive-to-negative charge ratios of PAGA/DNA complexes after 4, 8, and 24 hours of incubation at 37° C. respectively, the DNA/PAGA complexes degraded slowly over the course of 1 day until they were completely degraded. The higher stability of the complexes as compared to that of PAGA alone can be explained by the association of the amino groups of PAGA with the phosphate groups of the DNA. Moreover, partially degraded PAGA retained its ability to form complexes with DNA. Control PLL/DNA complexes were stable through 4 days under similar conditions (FIG. 3E).

EXAMPLE 4

Size and Structure of PAGA/DNA Complexes

Figure 4A:
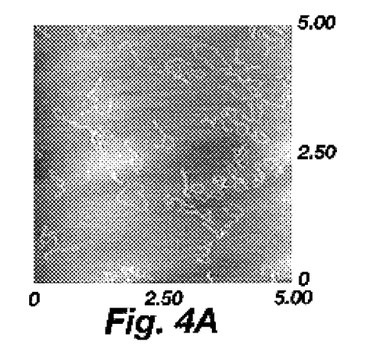
FIGS. 4A–H show atomic force microscopy(AFM) images of, respectively, (A) plasmid DNA (pSV-β-gal); (B), (C): PAGA/DNA complexes; (D) PAGA/DNA complex after 4 hr incubation; (E), (F): PAGA/DNA complex after 8 hr incubation; (G), (H) PAGA/DNA complex after 24 hr incubation at 37° C.
Figure 4B:
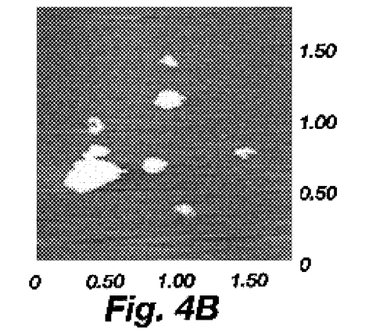
Figure 4C:
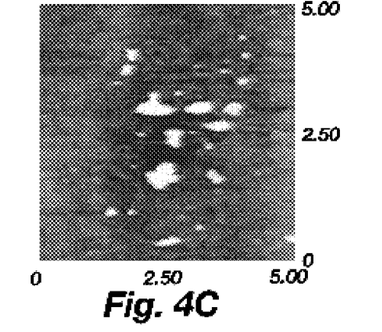

Atomic Force Microscopy(AFM) was used to assess the size and structure of the PAGA/DNA complexes. 2 μl of DNA (pSV-CAT, 5 μg/ml) in HEPES-Mg buffer (25 mM HEPES, 10 mM $MgCl_2$), and PAGA/DNA complexes, prepared according to the procedure of Example 3, made with 50 μg/ml were deposited onto freshly cleaved mica substrates, respectively. PLL/DNA complexes were treated similarly as controls. The solutions were allowed to adsorb for 2 minutes, and were then washed with 1 ml of distilled water and rapidly dried in a stream of $N_2$ gas. For PAGA/DNA complex and the degraded complex images, a complex was made by mixing pSV-β-gal plasmid solution (5 μg/ml in $H_2O$) with an equal volume of PAGA solution in $H_2O$. The complex solution was incubated at 37° C. to allow the degradation of the complex to occur. At an appropriate time interval, AFM image was obtained. AFM was performed using a Nanoscope IIIa equipped with a E scanner (Digital Instruments, Santa Barbara, Calif.). All AFM imaging was conventional ambient tapping mode. All the possible forms of plasmid DNA, super-coiled, nicked circular, and linear plasmid DNA can be seen in the AFM image (FIG. 4A). The size of naked plasmid DNA was determined to be about 1 μm. Formation of a self-assembling complex between PAGA and DNA can be seen in FIGS. 3B, C at charge rate (+/−) of 5:1. The shape of the complex was largely spherical but rather heterogeneous. After incubation of the complex at 37°

Figure 4D:
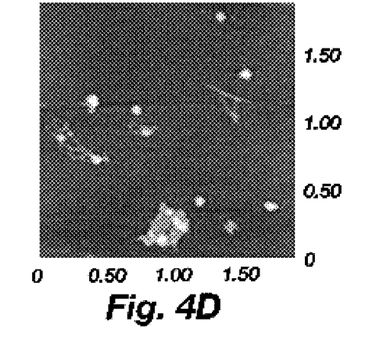
Figure 4E:
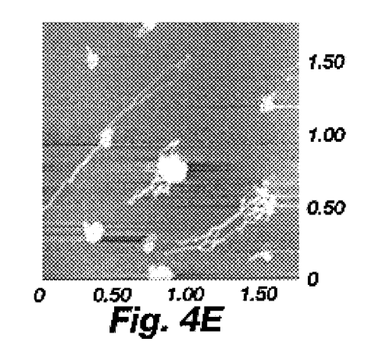
Figure 4F:
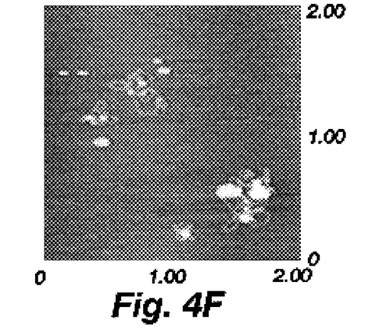
Figure 4G:
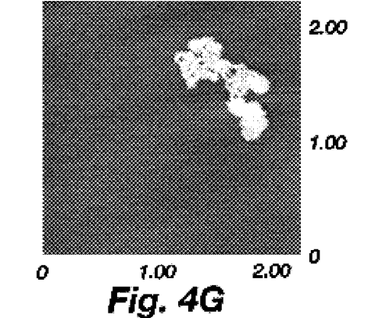
Figure 4H:
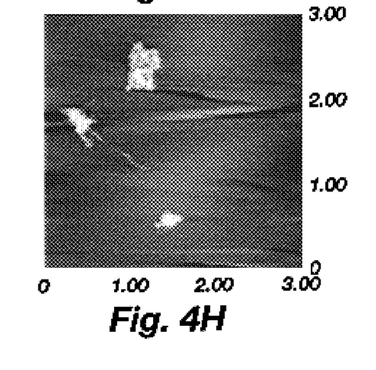

C. for 4 hours, the onset of degradation could be seen (FIG. 4D). A protruding DNA strand from dense cores could be seen with the shape of the dense cores becoming homogeneous and globular. The dense cores are thought to be condensed states. After 8 hours incubation, more of the DNA was released from the complex (FIGS. 4E, F). Two apparent characteristics of the 24 hour incubation images are that most of the DNA is released from the complex and that the density of the complex is significantly reduced (Figure, H). These results indicated that almost the entire DNA had been released from the complex. A slower degradation rate of the complex than for PAGA alone could be explained by the fact that ∈-amino groups in the polymer are blocked by DNA phosphate. Since only a few hours are required for the maximum transfection of cell, PAGA/DNA complex can be utilized as a stable complex system through cellular uptake.

The sizes of PAGA/DNA complexes were distributed from about 150 nm to about 250 nm, indicating that PAGA condenses DNA into a compact shape, as has been observed with other gene carrier systems. D.D. Dunlap et al., Nanoscopic Structure of DNA Condensed for Gene Delivery, 25 Nucleic Acids Res. 3095–3101 (1997); M. A. Wolfert et al., Characterization of Vectors for Gene Therapy Formed by Self-assembly of DNA with Synthetic Block Co-polymers, 7 Hum. Gene. Ther. 2123–2133 (1996). The shapes of the complexes were spherical and oblate, similar to that of PLL/DNA complexes.

EXAMPLE 5

Transfection Efficiency of PAGA/DNA Complexes

Transfection efficiency of PAGA/DNA complexes was evaluated using the 293 T cell line. This cell line was used previously to evaluate the transfection ability of poly (ethylene glycol)-PLL block copolymer. D.D. Dunlap et al., Nanoscopic Structure of DNA Condensed for Gene Delivery, 25 Nucleic Acids Res. 3095–3101 (1997). The 293 T cells were seeded at a density of $6\times10^4$ cells/well in a 24-well plate 24 hours prior to transfection. The PAGA carrier, prepared according to the procedure of Example 1, was dissolved in water just before being mixed with DNA to minimize its rapid degradation in aqueous solution. Plasmid PAGA/pSV-β-gal complexes were prepared by mixing pSV-β-gal (10 μg/ml; Promega) and PAGA in FBS-free cell culture medium and incubated for 20 minutes at room temperature. FES and chloroquine were added at final concentrations of 10% (v/v) and 100 μM, respectively. Medium in the 24-well plate was replaced with the transfection mixture followed by 4 hours of incubation at 37° C. Then, the transfection mixture was replaced with fresh medium. Cells were further incubated for 28 hours at 37° C. The b-galactosidase activity in transfected cells was determined using either the b-galactosidase enzyme assay system (Promega, Madison, Wis.) or in situ staining with X-gal. Promega Technical Bulletin No. 097, b-galactosidase Enzyme Assay System With Reporter Lysis Buffer (1996).

Figure 5A:
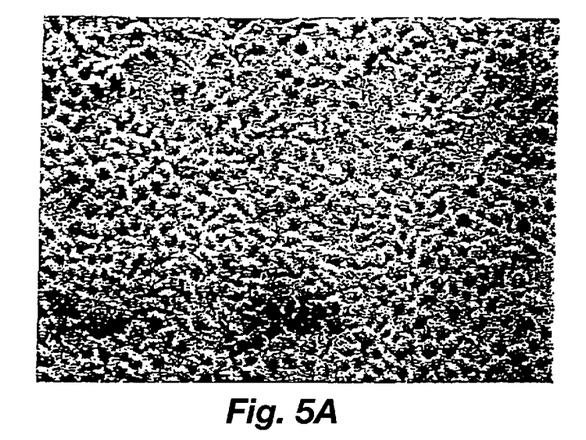
FIGS. 5A–D show transfection of 293 cells with PAGA/pSV-βgal complexes. 5A shows 5-bromo-4-chloro-3-indolyl-β-D-galactopyranoside (X-gal) staining of cells transfected with pSV-β-gal as a control. 5B and 5C show transfection with, respectively, pLL/pSV-β-gal complexes and PAGA/pSV-β-gal complexes. 5D shows transfection of PAGA/pSV-β-gal or PLL/DNA complex on 293 cells. Transfection efficiency was measured by expression of b-galactosidase activity using o-nitrophenyl-b-D-galactopyranoside (ONPG) as a substrate. Transfection protocol was optimized for each of the polymer and done in the presence of chloroquine (100 mM). The transfection efficiency of PLL/DNA was taken as 100%. The data are expressed as mean values of S experiments.
Figure 5B:
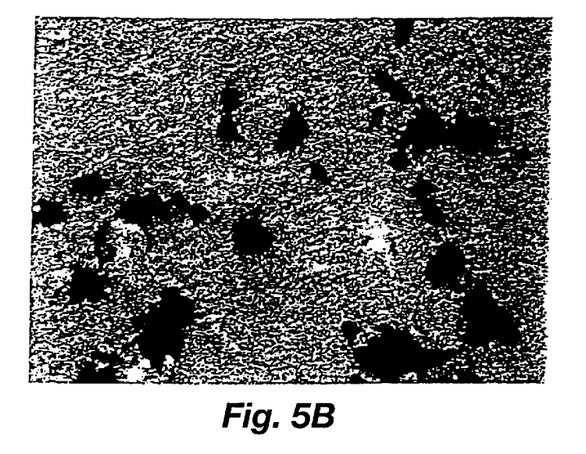
Figure 5C:
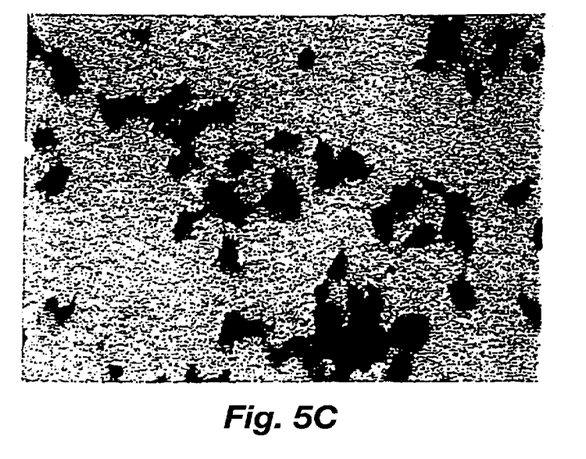

Notable transfection ability was observed at a 1:20 weight ratio of PAGA/pSV-β-gal complexes (FIG. 5A); the transfection efficiency of PAGA/DNA complexes was about twice that of control PLL/DNA complexes. FIGS. 5B–C shows that cells transfected with PAGA/pSV-β-gal complexes expressed the b-galactosidase enzyme as judged by in vitro staining. As shown by in situs staining, the transfected cells expressing b-galactosidase activity were stained blue. The cells themselves have no endogenous b-galactosidase activity.

Figure 5D:
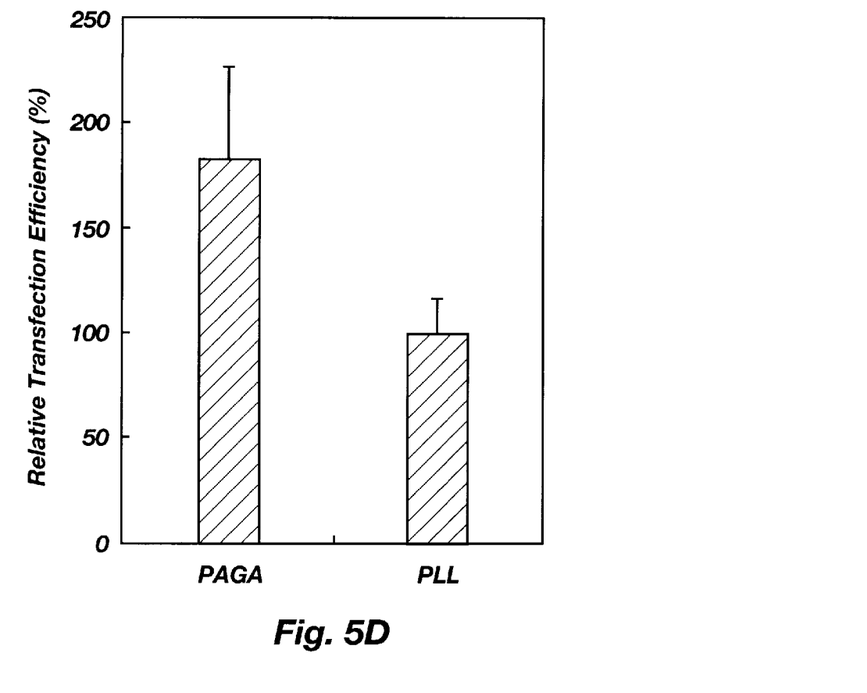

The transfection efficiency of the PAGA/DNA complex was also evaluated in vitro (FIG. 5D). PAGA show optimum transfection ability on 293 cells at a PAGA: DNA weight ratio of 10:1. The transfection efficiency of PAGA/DNA complex on 293 cells at an optimized condition was nearly twice that of PLL/DNA complex. The enhanced transfection efficiency of PAGA relative to that of PPL seems to be derived from the non-toxic nature of PAGA.

EXAMPLE 6

Toxicity of PAGA on Cells

Figure 6A:
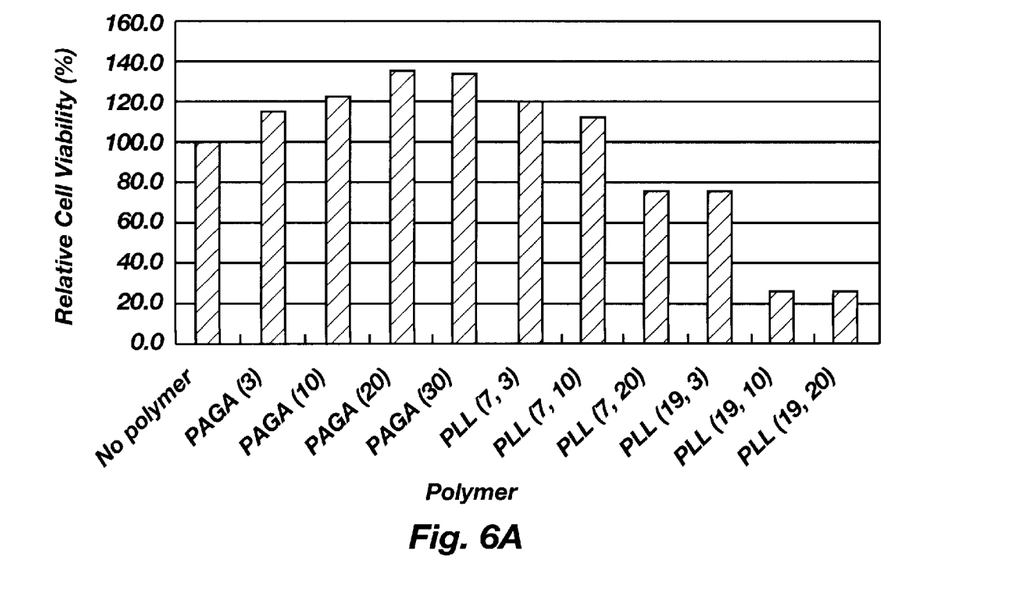
FIGS. 6A–B shows the results of the toxicity assay of PAGA on the cells using a 3-(4,5-dimethylthiazol-2-yl)-2.5-diphenyltetrazolium bromide (MTT) assay. Cell viabilities were assayed after 24 hours incubation of no polymer, PAGA, and PLL(MW 7K and 19K) at concentration of 30, 100 200 and 300 mg/ml, respectively. The viability of polymer-nontreated 293 cells was taken as 100%.
Figure 6B:
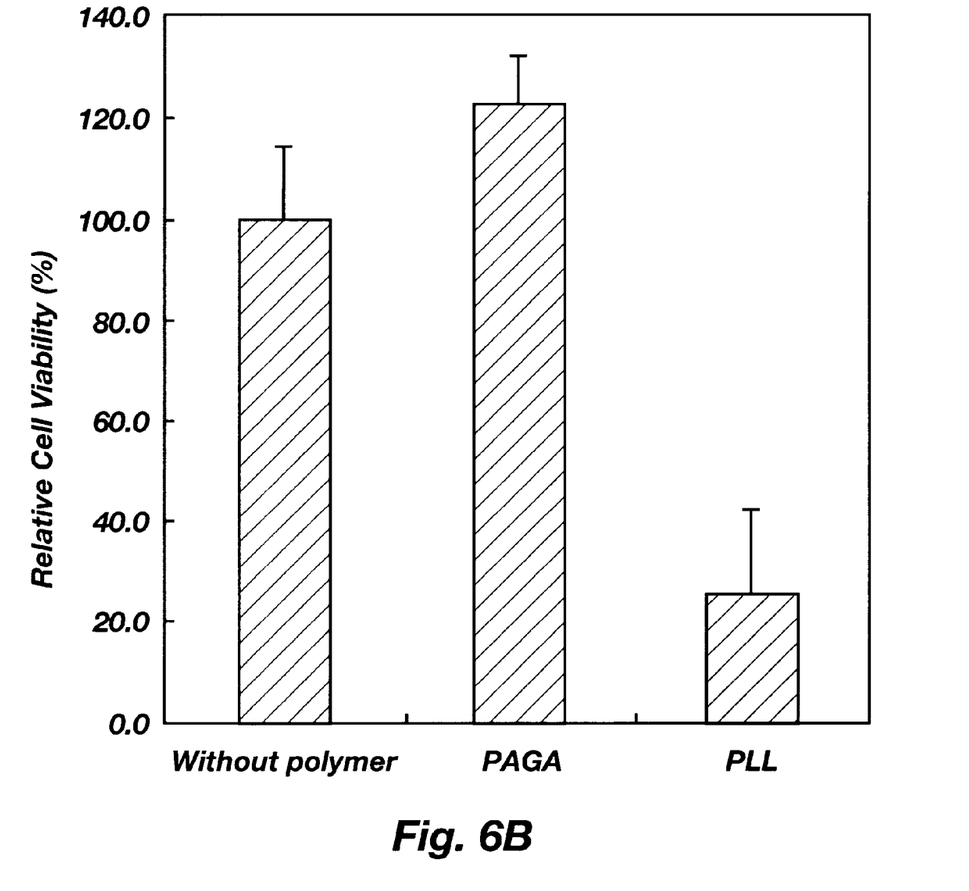

The toxicity of PAGA on the cells was assayed using a 3-(4,5-dimethylthiazol-2-yl)-2.5-diphenyl-tetrazolium bromide (MTT) assay. Mosman, T, Rapid calorimetric assay for cellular growth and survival: application to proliferation and cytotoxicity assays. 65 J. Immunol. Methods., 55–63 (1983). Cell viabilities were assayed after 24 hours incubation with no polymer, PAGA, and PLL(MW 7K and 19K) at concentrations of 30, 100 200 and 300 mg/ml, respectively. The viability of polymer-nontreated cells was taken as 100%. After incubating 293T cells for 24 hours with 100 μg/ml PAGA, the cells presented neither a decrease in cell population nor a cell morphology change. In contrast, cells incubated with PLL presented lower cell viability (25%), the cells granulated, and the cell population decreased at the same concentration (FIG. 6). At higher concentrations of PAGA, up to 300 μg/ml, there was still no significant cytotoxicity to the cells. There was a noticeably greater toxicity for some polymers applied in the absence of DNA (11) M. A. Wolfert et al., Hume. Gene Ther. 7,2121 (1996). In this regard, non-toxicity of PAGA without DNA complexation is noticeable. To the best of our knowledge, there is no gene carrier that does not display cytotoxicity without DNA complexation.

Therefore, PAGA of the present invention has the following characteristics: i) it is biodegradable with fast degradation in physiological conditions, but degradation becomes slowed down when it forms a complex with DNA; ii) the final degradation product is a natural product, L-oxylysine; iii) it condenses DNA with the overall shape of a sphere; iv) PAGA itself is not toxic; and v) the transfection efficiency of PAGA/DNA complex is about twice that of PLL/DNA complex. Fast degradation of PAGA will release free DNA into the nucleus so that the expression and transfection of DNA can be more effective.

The degraded fragments or monomer from PAGA, L-oxylysine, can be easily metabolized to carboxylic acid catalyzed by lysyl oxidase, and rapidly removed from cellular compartments followed by excretion or metabolism in the body. Several research papers indicated lysyl oxidase exists in human body. 37 Appl. Microbiol.Biotechnol. 599–603, (1992). Therefore, the utilitization of PAGA as a framework for a gene carrier that can be modified by the attachment of modular functions (e.g., a ligand for receptor-mediated endocytosis, an endosome disruptive function, or a nucleus localization signal) will likely result in safe gene therapy.

These examples are intended to be illustrative only and those skilled in the art will recognize, or be able to ascertain using no more than routine experimentation, many equivalents to the specific embodiments of the invention described herein. Such equivalents are intended to be encompassed by the following claims.

We claim:

1. Poly[α-(4-aminobutyl)-L-glycolic acid] (PAGA).

2. Poly[α-(4-aminobutyl)-L-glycolic acid](PAGA) of claim 1 wherein molecular weight of the PAGA is with a range of about 4,000 to 100,000 dalton.

3. A block copolymer comprising the PAGA of claim 2 copolymerized with a polymer selected from the group consisting of poly-L-lysine(PLL), polyargine, polyornithine, histones, avidin, protamines, polylactides and poly(lactide-co-glycolides) and mixed polymers thereof.

4. A block polymer according to claim 3 wherein the polymer is a member selected from the group consisting of poly-L-lysine(PLL), polyargine, polyornithine and mixed polymer thereof.

5. A composition for use as a gene delivery carrier comprising an effective amount of co-polymer of claim 4, admixed with an effective amount of a nucleic acid.

6. A composition of claim 5 said PAGA is covalently bound to an amphiphlilic polymer.

7. A composition of claim 6 wherein said amphiphilic polymer is a polyoxyalkyl glycol.

8. A composition of claim 7 wherein said polyoxyalkyl glycol is a member selected from the group consisting of polyethylene glycol homopolymers(PEG), methoxy polyethylene glycol homopolymers(MPEG), polypropylene glycol homopolymers, alpha-substituted poly(oxyalkyl) glycols, poly(oxyalkyl) glycol copolymers and block copolymers, and activated derivatives thereof.

9. A composition of claim 8 wherein said polyoxyalkyl glycol has a molecular weight of about 200 to 50,000.

10. A composition of claim 9 wherein said polyoxyalkyl glycol has a molecular weight of about 200 to 20,000.

11. A composition of claim 8 wherein the amphiphilic polymer is polyethylene glycol(PEG).

12. A composition of claim 5 further comprises a targeting moiety(TM), which is recognizable by a cell membrane receptor.

13. A composition of claim 12 wherein said targeting moiety(TM) is a member selected from a group consisting of: lactose, galactose, mannose, fructose, glucose, ribose, arabinose, xylose, rhamnose, peptides, chemotactic factors, hormones, natural metabolites, biotin, tetrahydrofolate, folic acid, lactobionic acid, asialo-oligosides, oligomannosides, phosphorylated oligomannosides, sulfated oligosaccharide of lactosamin, transferrin and asialoglycoprotein.

14. A composition of claim 5 wherein the nucleic acid comprising a DNA or RNA sequence encoding a gene to be delivered.

15. A composition of claim 14 wherein the nucleic acid comprising a DNA sequence encodes a genetic marker selected from the group consisting of luciferase gene, β-galactosidase gene, hygromycin resistance, and neomycin resistance, and chloramphenicol acetyl transferase.

16. A composition of claim 15 wherein the nucleic acid comprising a DNA sequence encodes a protein selected from the group consisting of low density lipoprotein receptors, coagulation factors, gene suppressers of tumors, major histocompatibility proteins, antioncogenes, p16, p53, thymidine kinase, IL2, IL 4, and TNFa.

17. A composition of claim 14 wherein the nucleic acid comprising a DNA sequence encodes a viral antigen.

18. A composition of claim 5 wherein the nucleic acid encodes an RNA selected from the group consisting of a RNA, an antisense RNA, and a ribozyme.

19. A composition of claim 5 wherein the nucleic acid encodes a lectin, a mannose receptor, a sialoadhesin, or a retroviral transactiviating factor (TAT).

20. A method of delivering a selected nucleic acid into a selected cell comprising the steps of:
(a) mixing an effective amount of the selected nucleic acid with an effective amount of poly[α-(4-aminobutyl)-L-glycolic acid](PAGA) or PAGA copolymer according to claim 4 to result in a complex;

(b) contacting the selected cell with the complex under conditions suitable to maintain the viability of the cell.

21. A method of transfecting cells comprising contacting said cells with the composition of claim 4 under conditions wherein said composition enters said cells, and the nucleic acid of said composition is released.

22. A method of claim 21 wherein said PAGA is covalently bound to an amphiphilic polymer.

23. A method of claim 22 wherein said amphophilic polymer is a polyoxyalkyl glycol.

24. A method of claim 23 wherein said polyoxyalkyl glycol is a member selected from the group consisting of polyethylene glycol homopolymers(PEG), methoxy polyethylene glycol homopolymers(mPEG), polypropylene glycol homopolymers, alpha-substituted poly(oxyalkyl) glycols, poly(oxyalkyl) glycol copolymers and block copolymers, and activated derivatives thereof.

25. A method of claim 24 wherein said polyoxyalkyl glycol has a molecular weight of about 200 to 50,000.

26. A method of claim 25 wherein said polyoxyalkyl glycol has a molecular weight of about 200 to 20,000.

27. A method of claim 26 wherein amphiphilic liner polymer is polyethylene glycol(PEG).

28. A method of claim 21 wherein the composition further comprises a targeting moiety (TM), and the cells to be transfected bear a receptor that recognizes the TM.

29. A method according to claim 28 wherein said targeting moiety(TM) is a member selected from the group consisting of: lactose, galactose, mannose, fructose, glucose, ribose, arabinose, xylose or rhamnose, peptides, chemotactic factors, hormones, natural metabolites, biotin, tetrahydrofolate, folic acid, lactobionic acid, asialo-oligosides, oligomannosides, phosphorylated oligomannosides, sulfated oligosaccharide of lactosamin, transferrin and asiologlycoprotein.

30. A method according to claim 29 wherein said TM is a member selected from the group consisting of: lactose, galactose, mannose, fructose, glucose, ribose, arabinose, xylose or rhamnose.

31. A method according to claim 30 wherein the nucleic acid comprising a DNA or RNA sequence encoding a gene.

32. A method according to claim 31 wherein the nucleic acid comprising a DNA sequence encodes a genetic marker selected from the group consisting of luciferase gene, β-galactosidase gene, hygromycin resistance, and neomycin resistance, and chloramphenicol acetyl transferase.

33. A method according to claim 31 wherein the nucleic acid comprising a DNA sequence encodes a protein selected from the group consisting of low density lipoprotein receptors, coagulation factors, gene suppressers of tumors, major histocompatibility proteins, antioncogenes, p16, p53, thymidine kinase, IL2, IL 4, and TNFa.

34. A method according to claim 31 wherein the nucleic acid comprising a DNA sequence encodes a viral antigen.

35. A method according to claim 31 wherein the nucleic acid encodes an RNA selected from the group consisting of a sense RNA, an antisense RNA, and a ribozyme.

36. A method according to claim 31 wherein the nucleic acid encodes a lectin, a mannose receptor, a sialoadhesin, or a retroviral transactiviating factor (TAT).

37. A method for making poly[α-(4-aminobutyl)-L-glycolic acid] comprising the steps of:
(a) protecting the ∈-amino group of L-lysine with an amine blocking agent to result in blocked L-lysine;
(b) deaminating the α-amino group of blocked L-lysine to result in blocked (6-amino2-(S)-hydroxyhexanoic acid);

(c) polymerizing the blocked (6-ainino-2(S)-hydroxyhexanoic acid) to result in blocked poly [α-(4-aminobutyl)-L-glycolic acid]; and (d) deprotecting the blocked poly[α-(4-aminobutyl)-L-glycolic acid] by removing the amine blocking group to result in poly[α-(4-aminobutyl)-L-glycolic acid].

38. A drug delivery composition comprising an effective amount of poly[α-(4-aminobutyl)-L-glycolic acid](PAGA) complexed with an effective amount of a negatively charged molecule.

39. A drug delivery composition according to claim 38 wherein said drug composition is a biodegradable particulate.

40. A drug delivery composition according to claim 39 wherein the biodegradable particulate is a nanoparticle or a microsphere.

41. A drug delivery composition according to claim 40 wherein the negatively charged molecule is a peptide, protein, or non-soluble drug molecules.

* * * * *